US006467330B1

(12) United States Patent
Vizintin et al.

(10) Patent No.: US 6,467,330 B1
(45) Date of Patent: Oct. 22, 2002

(54) APPARATUS FOR TESTING PHYSICAL CHARACTERISTICS, ESPECIALLY ROLLING CONTACT FATIGUE RESISTANCE OF MATERIALS

(76) Inventors: Joze Vizintin, Azmanova 34, 1000 Ljubljana (SI); Mitjan Kalin, Cankarjeva 24, 5000 Nova Gorica (SI)

( * ) Notice: Subject to any disclaimer, the term of this patent is extended or adjusted under 35 U.S.C. 154(b) by 0 days.

(21) Appl. No.: 09/456,154

(22) Filed: Dec. 7, 1999

(30) Foreign Application Priority Data

Jan. 15, 1999 (SI) .................................................. 9900004

(51) Int. Cl.$^7$ ................................................ G01N 3/56
(52) U.S. Cl. ............................................................. 73/7
(58) Field of Search .............................. 73/7, 8, 865.3, 73/808, 813, 815, 817, 822, 81, 82, 9, 818

(56) References Cited

U.S. PATENT DOCUMENTS

| 2,962,890 A | * 12/1960 | Borrino ............................ 73/7 |
| 3,041,868 A | * 12/1960 | Schaschl et al. ................. 73/7 |
| 4,452,065 A | 6/1984 | Minter |
| 5,101,655 A | * 4/1992 | Mueller ............................ 73/7 |
| 5,969,226 A | * 10/1999 | Wert et al. ....................... 73/7 |

OTHER PUBLICATIONS

Soviet Inventions Illustrated, Section E1., Week 8625, Derwent London, Class S03, AN 86–160934, SU 1191 776A (Drozdov); Nov. 15, 1985.
Soviet Inventions Illustrated, Section E1., Week 8536, Derwent London, Class S03, AN 85–221642, SU 1087 822A (Rost Agr.); Apr. 23, 1985.
Soviet Inventions Illustrated, Section E1., Week 8345, Derwent London, Calss S03, AN 83–813912, SU 991–255A (Zaporo M.); Jan. 23, 1983.
Soviet Inventions Illustrated, Section E1., Week 8328, Derwent London, Class S03, AN 83–710799, SU 957 056A (Odintsov); Sep. 17, 1982.

* cited by examiner

Primary Examiner—Robert Raevis
(74) Attorney, Agent, or Firm—Jackson Walker, L.L.P.

(57) ABSTRACT

The present apparatus for testing rolling physical characteristics of materials, especially rolling contact fatigue resistance of materials, represents the most simple and universal solution, by which it is possible to test not only laboratory tested objects prepared in advance, but also various final products or parts thereof. Thanks to linearly oscillating movement of the testing ball 30 foreseen by the apparatus according to the invention, it is much easier to test the surface 20 of the tested object 2. While appropriate point contact between the testing ball 30 and appropriate surface 20 of the tested object 2 is ensured, the testing ball 30 is linearly oscillatory rolled here and there along the surface 30 of the tested object 2, which is thereby clamped in appropriate clamping unit 1. The loading unit of the present invention comprises a bearing surface 33 arranged opposite to the tested object 2 and is equipped with a groove 34 arranged in the direction of rolling of the testing ball 30. The groove being capable of guiding the testing ball 30 over the testing surface of the tested object.

1 Claim, 1 Drawing Sheet

Figure 1:
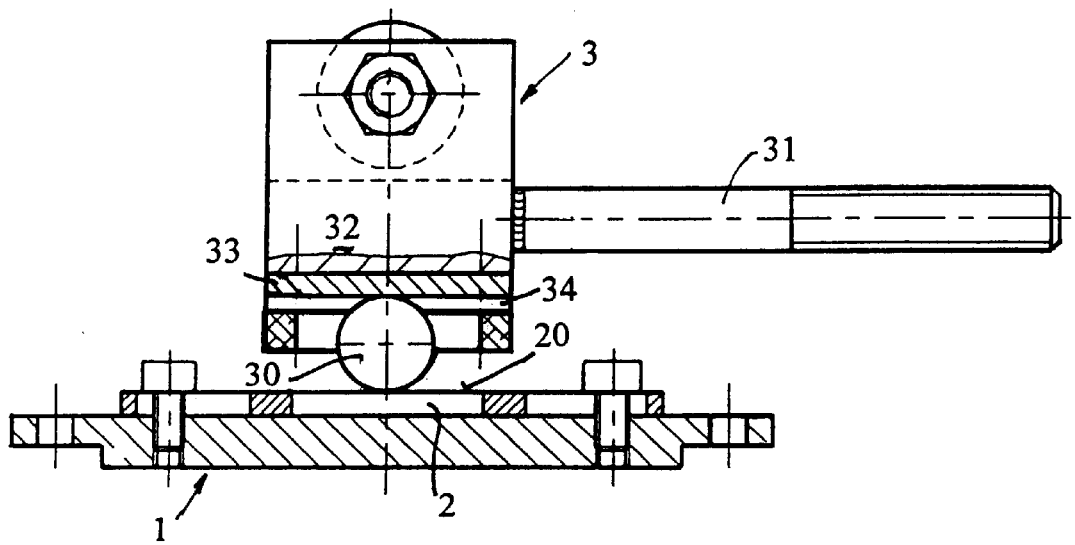

APPARATUS FOR TESTING PHYSICAL CHARACTERISTICS, ESPECIALLY ROLLING CONTACT FATIGUE RESISTANCE OF MATERIALS

The present invention relates to an apparatus for testing physical characteristics of materials, especially for testing rolling contact fatigue resistance of materials. While using such an apparatus and thereby testing rolling contact fatigue resistance of certain material, a spherical tester, namely a testing ball, is rolled along a surface of a tested object under appropriate loading, whereby a certain number of repeats has to be executed and appropriate point contact between the aforementioned testing ball and the surface of the tested object has to be ensured.

The aim of the present invention is to create as much as possible simple apparatus, which shall be useful for testing the rolling contact fatigue resistance of materials and by which as much as possible various testing possibilities shall be available, so that in despite of testing of ordinary laboratory tested objects prepared in advance also quite satisfactory testing of different final products or parts thereof would be possible.

As known to those skilled in the art (and as e.g. shown in the technical description of the available testing apparatuses manufactured by FAG Kugelfischer Georg Schäfer AG), the common used apparatuses for testing rolling contact fatigue resistance of materials mainly comprise a clamping unit, a loading unit and a driving assembly. However, with regard to discussion relating to the features of the present invention, the most important part is the loading unit, which is created as to enable placing the testing ba of appropriate diameter into a suitable bearing, by which the ball is placed in such a manner that it can rotate freely in all directions. In addition, the loading unit itself is also rotatable, so that the bearing and herewith also the testing ball can be revolved around the axis, whereby as a consequence appropriate movement of the testing ball is obtained in appropriate plane, namely cyclical movement along a circular trajectory of appropriate diameter. Furthermore, the loading unit is arranged to ensure certain loading, to which the testing ball is exposed while abutting the tested object. The clamping unit of such an apparatus is arranged for receiving and reliable clamping the tested object, particularly with regard to aforementioned loading of the testing ball as well as with respect to circular movement thereof during testing. The driving assembly comprises suitable driving and bearing parts, which at the defined loading of the testing ball on the surface of each tested object enable a suitable circulating of the testing ball on the surface of each tested object, clamped in the clamping unit.

Such an apparatus is relatively complicated, but in common it enables testing of the rolling contact fatigue resistance of materials. Nevertheless, in order to enable testing of certain material, a special tested object of appropriate material must be available, which comprise appropriate surface, which has to be large enough to enable circular movements of the testing ball on the surface of the tested object, whereby a certain number (e.g. several hundred thousands or even several millions) of cycles of rolling appropriate loaded testing ball along the surface of the tested object in a point contact between them is expected.

Such an apparatus should be used either for laboratory testing where appropriate tested objects prepared specially for this purpose are used, or even for testing of final products or e.g. assembling parts thereof, which may also be important in the industry. In certain cases, especially when testing certain materials (e.g. ceramics, noble and precious metals or similar) also the laboratory testing as such may involve various and serious problems. On the other hand, when testing different final products or parts thereof (except e.g. by testing of roll bearings or parts thereof) by such an apparatus, it is ordinary really difficult or quite impossible to find appropriate surface, which would be suitable for eccentrically turning and rolling a testing ball, as well as to ensure appropriate clamping of the tested object simultaneously.

According to the invention, an apparatus for testing physical characteristics of materials, especially rolling contact fatigue resistance of materials, comprises a loading unit, which is connected to a driving assembly and driven by it in such a manner, that a linear oscillatory movement of the loading unit is enabled, whereby appropriate tester, namely a testing ball, is rolled along the surface of a tested object, which is held in a clamping unit. Thereby, a loading unit preferably comprises a screw-rod, by means of which it can be connected to appropriate crank mechanism, which is furthermore connected to appropriate driving assembly and driven by it. While the point contact between the tester and tested object is ensured, the aforementioned testing ball can be linearly oscillatory rolled here and there along the surface of the tested object, by which the said testing ball is moreover loaded in appropriate manner by means of the loading unit comprising a bearing surface arranged adjacent to the tested object and equipped by a groove arranged in a rolling direction of the testing ball, whereby in the said groove the testing ball is placed.

Figure 2:
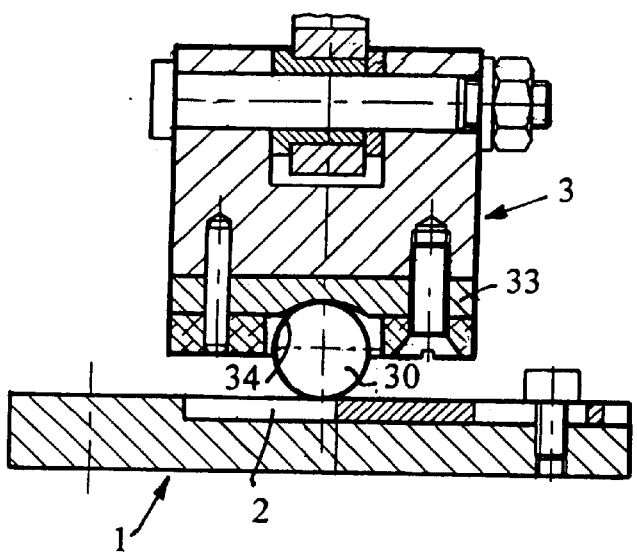

Now, the invention will be explained in more detail by means of an embodiment, shown in the enclosed drawing, where FIG. 1 is a front view of an apparatus for testing physical characteristics of materials, especially rolling contact fatigue resistance of materials; and FIG. 2 is a side view of the apparatus as shown in FIG. 1.

Apparatus for testing physical characteristics of materials, namely rolling, contact, fatigue, resistance thereof, comprises a clamping unit 1 suitable for clamping a tested object 2, and a loading unit 3, which comprises a freely rotatable testing ball 30, which can be exposed to appropriate loading and rest towards the surface 20 of the tested object 2 and is moreover simultaneously also rolled along this surface 20. Thereby, appropriate point contact between the testing ball 30 and the surface 20 of the test object is ensured. The apparatus furthermore comprises a driving assembly 31 capable of enabling suitable movement of the loading unit 3 and herewith appropriate movement of the testing ball 30 along the surface 20 of the tested object 2. In one embodiment, the driving assembly 31 may be any device capable of moving the loading unit 3 in a linear, oscillating manner.

The testing ball 30 is linearly oscillatory rolled here and there along the surface 20 of the tested object 2, while the said point contact between them is ensured and while the tested object 2 is firmly clamped in the clamping unit 1 and where the ball 30 is at the same time loaded by means of the loading unit 3, which comprises a bearing surface 33 positioned opposite to the tested object 2. The bearing surface 33 comprises a groove 34, which is arranged in the rolling direction of the testing ball 30 and positioned in the direction of the testing surface 20 such that the groove 34 extends parallel to the testing surface. The testing ball 30 may be placed and supported in such a manner that is can also be rolled here and there along the groove 34 itself. Placement of the testing ball 30 within the groove 34 allows the testing ball 30 to roll freely along the testing surface 20, such rolling being facilitated by friction forces between 1) the testing ball 30 and the groove 34 and 2) the testing ball 30 and the testing surface 20 of the tested object 2. Thus, placement of the ball 30 within the groove 34 instead of attachment of the ball 30 to the loading unit allows free rotation of the ball due to frictional forces.

According to the invention such a satisfactory solution of the testing apparatus is possible mainly thanks to the fact, that the loading unit 3 is connected to appropriate driving assembly 31 and driven by it in such a way that a linearly oscillatory movement of the loading unit 3 is achieved and consequently also of the testing ball 30 along the surface 20 of the tested object 2, which is clamped thereby in the clamping unit 1. To this aim, the driving assembly is equipped with a screw-rod (not shown), by which it is joinable to appropriate crank mechanism (not shown), which is connected to a suitable driving assembly and driven herewith.

In such a way, a simple and universal testing apparatus was realised, by which it is possible not only testing of materials on the surfaces of special tested objects prepared in advance for laboratory purposes, but also testing of different final products or parts thereof, where a relatively small area required for linearly oscillatory movement of the testing ball 30 can be found and defined much easier as e.g. those for circular movement as required before.

What is claimed is:

1. An apparatus for testing rolling contact fatigue resistance of materials comprising:

a loading unit capable of reciprocating motion, said loading unit having a freely rotatable testing ball for rolling along a testing surface of a tested object, said loading unit having a bearing surface positioned opposite of said tested object, said bearing surface further comprising a groove defining a rolling position of said testing ball, said groove positioned upon said bearing surface in the direction of said tested object such that said groove extends parallel to said testing surface of said tested object, said testing ball being partially surrounded by said bearing surface of said loading unit when said testing ball is placed within said groove, placement of said testing ball within said groove allowing rotational motion of said testing ball along said testing surface to be facilitated by 1) friction forces between said testing ball and said groove and 2) friction forces between said testing ball and said testing surface;

a driving assembly connected to said loading unit, said driving assembly capable of driving said loading unit; and a clamping unit for holding said tested object in a stationary position during testing.

\* \* \* \* \*